(12) United States Patent
Aoki

(10) Patent No.: US 7,145,113 B2
(45) Date of Patent: Dec. 5, 2006

(54) HEATING DEVICE

(75) Inventor: Yukihiro Aoki, Okaya (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/890,208

(22) Filed: Jul. 14, 2004

(65) Prior Publication Data

US 2005/0016992 A1   Jan. 27, 2005

(30) Foreign Application Priority Data

Jul. 24, 2003   (JP)   ............................. 2003-278727

(51) Int. Cl.
*H05B 3/16* (2006.01)
(52) U.S. Cl. ...................................... 219/543; 219/544
(58) Field of Classification Search ................ 219/543, 219/542, 544, 444.1, 216, 465.1, 22 R, 530, 219/540; 338/22 R
See application file for complete search history.

(56) References Cited

U.S. PATENT DOCUMENTS

| | | | |
|---|---|---|---|
| 2,600,458 A | 6/1952 | Cox ............................. 219/19 |
| 3,520,053 A | 7/1970 | Hinton et al. .................. 29/611 |
| 4,104,506 A * | 8/1978 | Phillips ................... 219/85.15 |
| 4,147,927 A | 4/1979 | Pirotte ......................... 219/541 |
| 4,346,277 A * | 8/1982 | Wojtecki et al. ............. 219/528 |
| 4,834,863 A * | 5/1989 | Yamada et al. ............. 204/429 |
| 5,055,859 A * | 10/1991 | Wakabayashi et al. ....... 347/209 |
| 5,057,811 A * | 10/1991 | Strott et al. ................ 338/22 R |
| 5,313,943 A | 5/1994 | Houser et al. .............. 128/642 |
| 5,359,179 A * | 10/1994 | Desloge et al. ............. 219/535 |
| 5,560,851 A * | 10/1996 | Thimm et al. .............. 219/543 |
| 5,576,748 A * | 11/1996 | Tamura ........................ 347/58 |
| 5,641,990 A * | 6/1997 | Chiu ........................... 257/737 |
| 6,054,691 A * | 4/2000 | McGwire .................... 219/535 |
| 6,114,661 A * | 9/2000 | Leung ......................... 219/222 |
| 6,645,360 B1 * | 11/2003 | Eisele et al. ................ 204/426 |

FOREIGN PATENT DOCUMENTS

| | | |
|---|---|---|
| EP | 0 026 457 | 4/1981 |
| GB | 2076747 A * | 12/1981 |
| JP | 9-322901 A | 12/1997 |

OTHER PUBLICATIONS

European Search Report dated Nov. 10, 2004 for the corrresponding European patent application No. EP 04 01 6362.

* cited by examiner

*Primary Examiner*—Robin O. Evans
*Assistant Examiner*—Vinod Patel
(74) *Attorney, Agent, or Firm*—Westerman, Hattori, Daniels & Adrian, LLP.

(57) ABSTRACT

A heating device is constructed such that a heating member made of nickel-chromium or a high melting point metal is held in an electrically insulating member made of an oxide or nitride, and a solder connecting layer consisting of a nickel layer serving as buffer layer and a nickel plating layer serving as solder uniting layer is formed on a surface of the electrically insulating member corresponding to a slender portion of the heating member. An adhesion between the solder connecting layer and the electrically insulating member holding the heating member is thereby improved so that the heating device is achieved as having a high reliability and at the same time as capable of improving heat conducting performance from the heating member to a heated body.

7 Claims, 6 Drawing Sheets

HEATING DEVICE

This application claims benefit of Japanese Patent Application No.2003-278727 filed in Japan on Jul. 24, 2003, the contents of which are incorporated by this reference.

BACKGROUND OF THE INVENTION

The present invention relates to heating device to be adhered through a soft solder or a hard solder material layer to a heated body to supply heat thereto, and more particularly relates to the construction of a heating section of the heating device.

A heating device using a high melting point metal film resistance heater is disclosed in Japanese Patent Application Laid-Open Hei-9-322901 as for cautery hemostasis device to be used as an endoscopic treatment tool. FIGS. 1 and 2 are a perspective view and a side sectional view, respectively, showing a heating section of the heating device as disclosed in the above publication with omitting a portion thereof to indicate its interior. FIG. 3 is a sectional view along line A–A' in FIG. 1. FIG. 4 is a side view showing the heating section of the heating device in its state joined to a heated body.

In the heating device disclosed in the above publication as shown in FIGS. 1 and 2, an electrically insulating material, preferably an electrically insulating layer 102 having a thickness of 0.3 μm to 100 μm made of high-molecular material such as silicon dioxide or polyimide is formed on and adhered to one main surface of a heating device substrate 101 having a thickness of 0.2 mm to 3.0 mm made of a semiconductor or silicon dioxide or ceramics. The electrically insulating layer 102 serving as an insulating member becomes unnecessary when the heating device substrate 101 is dielectric.

As shown in FIG. 3, a heating layer 103 made of a high melting point metal film having a thickness of 0.1 μm to 50 μm for example of patterned titanium, molybdenum or tungsten or of an alloy film of such high melting point metals is formed on and adhered to the electrically insulating layer 102. A portion to be heated of the heating layer 103 is narrowed to a line width of 0.1 μm to 100 μm to provide high resistance so as to facilitate its localized heat generation. A wiring layer 104 having a thickness of 0.1 μm to 50 μm of a low resistance metal film for example of patterned aluminum or copper or of an alloy film of such low resistance metals is formed on and adhered to the heating layer 103 and electrically insulating layer 102, and a contacting portion between the heating layer 103 and the wiring layer 104 is electrically connected. The reason for providing the wiring layer 104 is to prevent heat generation due to electric conduction at a center portion of the heating device substrate 101.

A heat conducting and electrically insulating layer 105 having a thickness of 0.3 μm to 50 μm of a material such as aluminum nitride or aluminum oxide having a relatively high thermal conductivity as an electrically insulating material is formed on and adhered to the portion to be heated on the heating layer 103. Then an electrically insulating layer 106 having a thickness of 0.3 μm to 100 μm is formed on and adhered to an edge portion 105a of the heat conducting and electrically insulating layer 105, and the wiring layer 104 and electrically insulating layer 102.

In the case where a high-temperature resisting solder is used as the adhering technique of the heated body to the heating device, a solder connecting layer 107 using a metal material such as nickel is provided on the heat conducting and electrically insulating layer 105 to secure adhesion of the solder. Here a metal material such as nickel is to be simply used as the heating device side solder connecting layer 107.

As shown in FIG. 4, an adhering layer 109 of a material such as a high-temperature resisting solder or an adhesive that resists high temperatures and has a favorable thermal conductivity is provided between the heated body 108 and the solder connecting layer 107 to facilitate heat conduction from the heating section of the heating device to the heated body 108.

SUMMARY OF THE INVENTION

It is an object of the present invention to provide a heating device having a heating section in which adhesion between a solder connecting layer and an electrically insulating member held between the solder connecting layer and a heating member is improved so that peeling off of the solder connecting layer is made less likely to provide a high reliability and at the same time a heat conducting performance from the heating member to a heated body is improved.

There is provided a heating device in accordance with a first aspect of the invention, including a heating member held in an electrically insulating member and a solder connecting layer formed on a surface of the electrically insulating member, the solder connecting layer having a laminated structure.

In a second aspect of the invention, the solder connecting layer in the heating device according to the first aspect includes at least one buffer layer and a solder uniting layer.

In a third aspect of the invention, the buffer layer in the heating device according to the second aspect is a metal layer.

In a fourth aspect of the invention, the solder uniting layer in the heating device according to the second or third aspect is a nickel plating layer or copper plating layer.

In a fifth aspect of the invention, the solder connecting layer in the heating device according to any one of the first to fourth aspects is formed on least one side of the electrically insulating member.

DESCRIPTION OF THE PREFERRED EMBODIMENTS (Embodiment 1)

Figure 1:
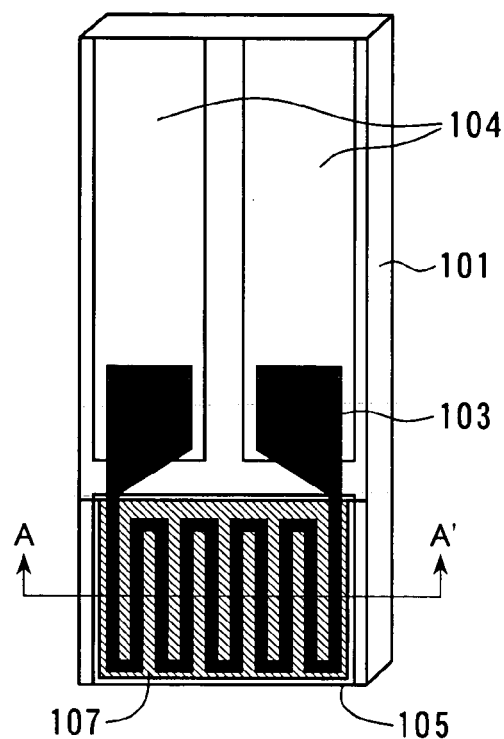
FIG. 1 is a perspective view showing the construction of a heating section of the prior-art heating device.
Figure 2:
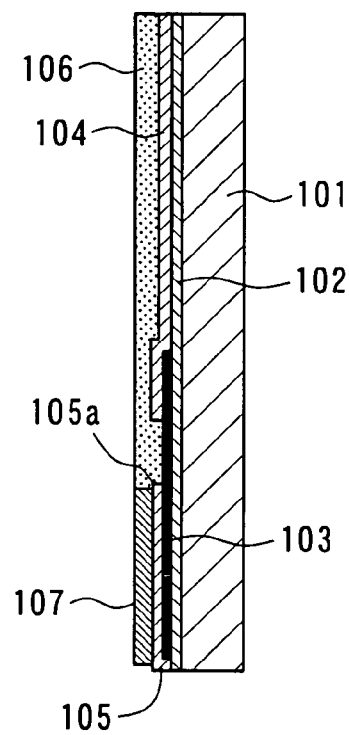
FIG. 2 is a side sectional view of the prior-art example shown in FIG. 1.
Figure 3:
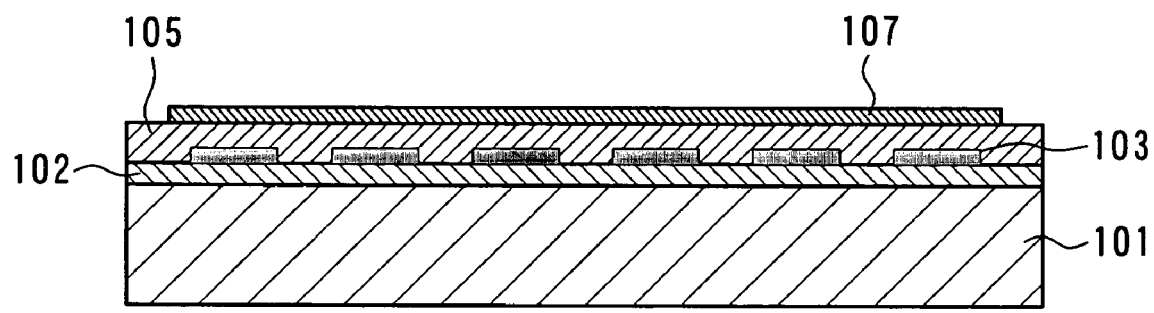
FIG. 3 shows a section along line A–A' in the prior-art example shown in FIG. 1.
Figure 4:
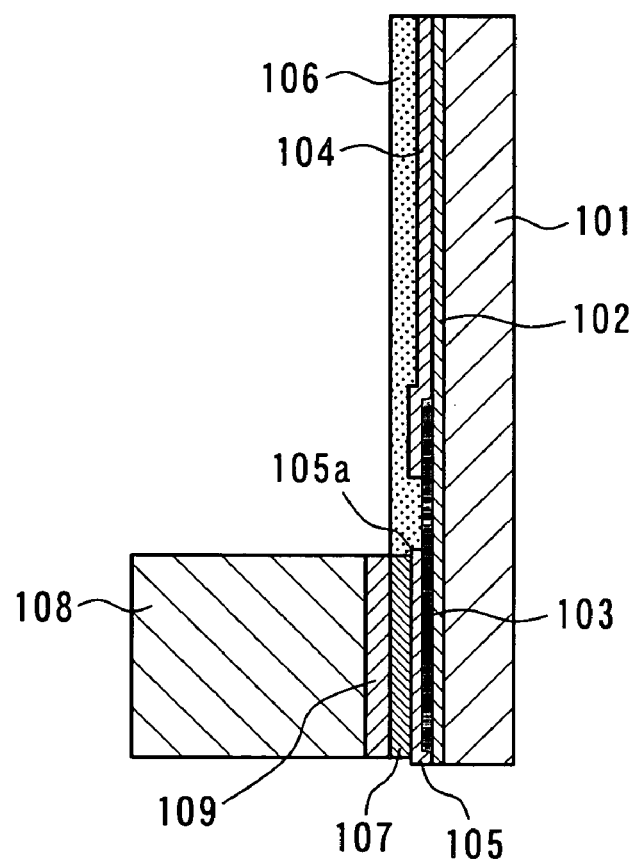
FIG. 4 shows the manner of joining a heated body to the heating section of the prior-art heating device shown in FIG. 1.
Figure 5:
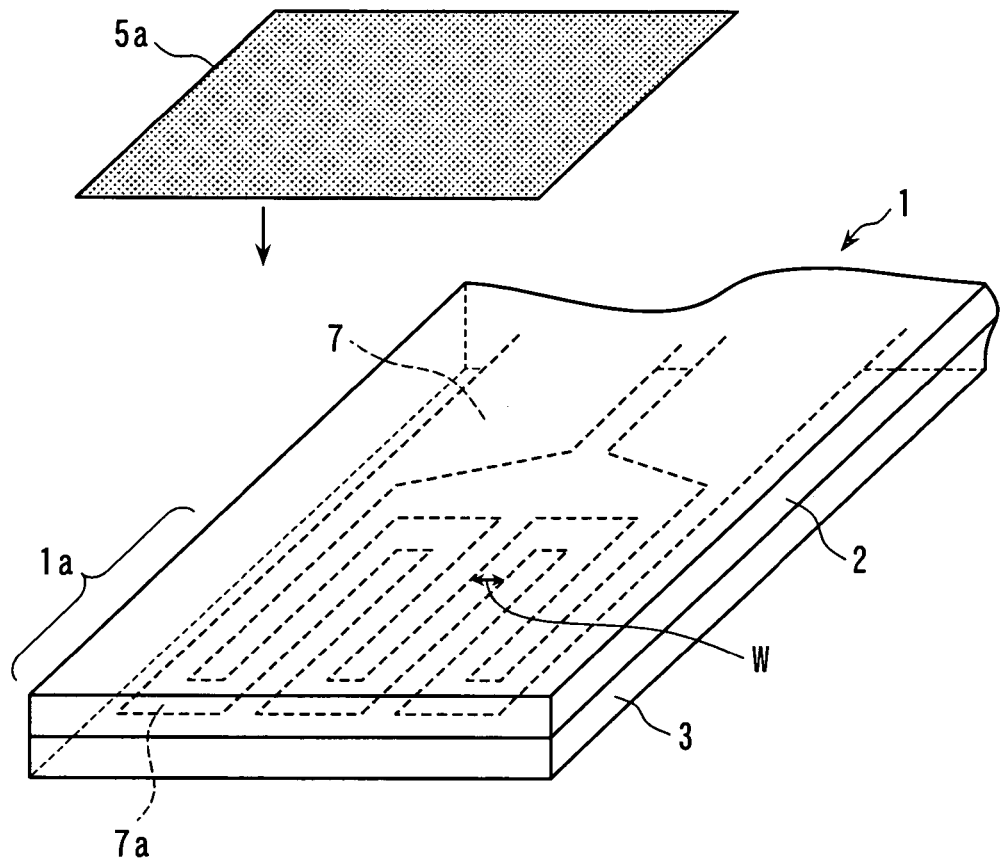
FIG. 5 is a perspective view showing the construction of heating section of a first embodiment of the heating device according to the invention with separating a solder connecting layer therefrom.
Figure 6:
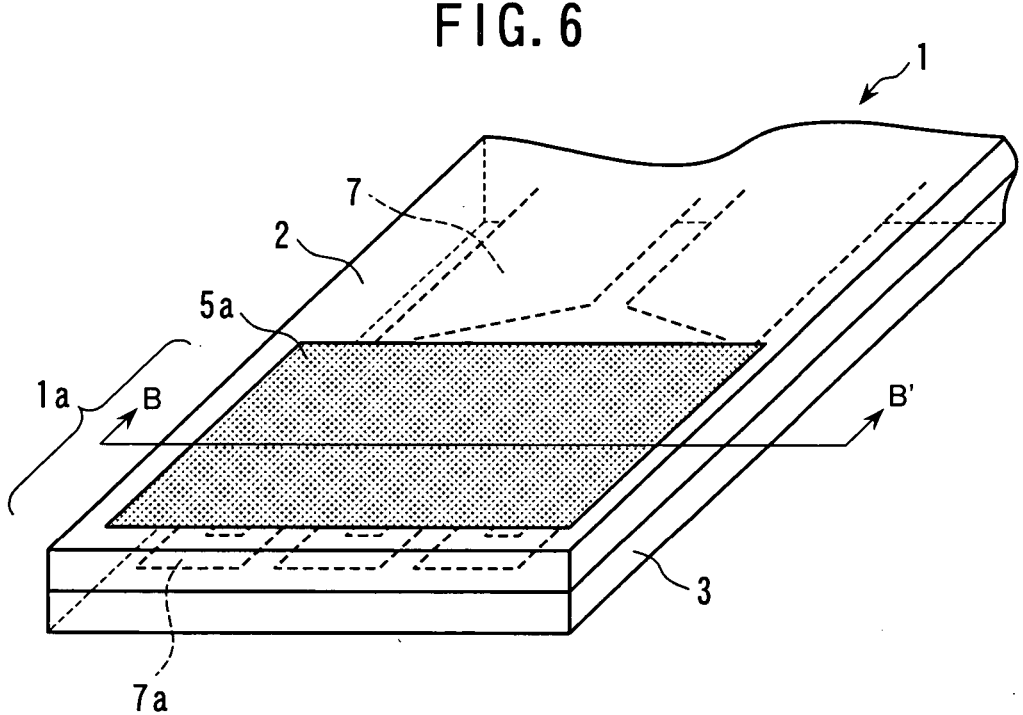
FIG. 6 is a perspective view showing the construction of the heating section of the heating device according to the first embodiment shown in FIG. 5 with the solder connecting layer joined thereto.

A description will be given below of the best mode for carrying out the invention with reference to the drawings. A first embodiment will now be described. FIGS. 5 and 6 each are a perspective view showing the construction of a heating section 1a of a heating device 1 according to the first embodiment, with a solder connecting layer 5a in FIG. 5 shown in a manner separated therefrom. Referring to FIGS. 5 and 6, numerals 2 and 3 each denote an electrically insulating member made of an oxide or nitride. Numeral 7 denotes a heating member for example made of nickel-chromium or a high melting point metal such as molybdenum or tungsten which is held between the electrically insulating members 2 and 3. It is narrowed in its width W and at the same time elongated within the heating section 1a so as to form a grid-like slender section 7a. The reason for using such configuration is to increase the resistance value within the heating section 1a so as to facilitate heat generation. The heating device 1 is constructed by further forming a solder connecting layer 5a of the heating section 1a on a surface of the electrically insulating member 2 corresponding to the slender section 7a of the heating member 7. Here, the solder connecting layer 5a may either be of the same size corresponding to the heating section 1a or be formed to extensively cover the heating section 1a. It should be noted that, for ease of explanation, the electrically insulating members 2 and 3 in FIGS. 5 and 6 (and hereinafter) are indicated as transparent matters.

Figure 7:
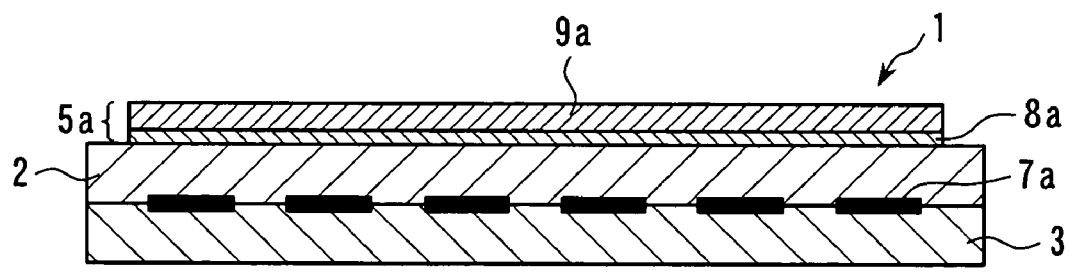
FIG. 7 shows a section along line B–B' of FIG. 6.

A cross sectional structure of the heating section 1a will now be described. FIG. 7 is a sectional view along line B–B' in the heating device shown in FIG. 6. As shown in FIG. 7, a nickel layer 8a serving as buffer layer and a nickel plating layer 9a serving as solder uniting layer are formed so as to constitute the solder connecting layer 5a on a surface of the electrically insulating member 2 in which the heating member 7 is held. Here the nickel layer 8a serving as buffer layer has a role for securing adhesion to the electrically insulating member 2 and a role of being a base for forming a film of the nickel plating layer 9a which is to be formed by an electrolytic or electroless method to be described later. In particular, the nickel layer 8a forms nickel oxides or nickel nitrides at the portion of contact with the electrically insulating member 2 which is made for example of an oxide or nitride. These improve adhesion between the nickel layer 8a and the electrically insulating member 2 and thus act to prevent peeling of the solder connecting layer 5a. Further, nickel layer 8a is suitable also as the base for forming a film of the nickel plating layer 9a and, since their main components are the same metal, a favorable adhesion is provided between the nickel layer (buffer layer) 8a and the nickel plating layer (solder uniting layer) 9a.

A method for forming the solder connecting layer 5a will be briefly described below. First, on a surface of the electrically insulating member 2 of the heating device 1 corresponding to the heating section 1a, a nickel layer 8a having a thickness of 10 nm to 500 nm is formed as a buffer layer by means of evaporation or sputtering method. At this time, the patterning of the nickel layer (buffer layer) 8a is effected by the method in which deposition and patterning are concurrently effected at the time of evaporation or sputtering by using a shielding mask patterned into a desired configuration or by the method in which, after depositing a nickel layer (buffer layer) all over the surface of the electrically insulating member 2, photoetching is effected to form the nickel layer 8a. It is desirable to effect plasma cleaning on the surface of the electrically insulating member 2 by an inert gas such as argon immediately before the forming of the film of the nickel layer 8a. The reason for this is to remove impurities which hamper the adhesion between the nickel layer (buffer layer) 8a and the electrically insulating member 2.

Subsequently, a boron-contained nickel plating layer (hereinafter abbreviated as Ni—B layer) 9a is formed to a thickness of 500 nm to 50 µm by an electrolytic or electroless method on the nickel layer 8a. The reason for this is that boron contained in the Ni—B layer makes less likely an occurrence of corrosion at the time of heat generation of the electrically insulating members 2 and 3 which are made for example of silicon nitride, aluminum nitride or aluminum oxide. It is desirable to effect plasma cleaning by an inert gas such as argon on the surface of the nickel layer (buffer layer) 8a immediately before the forming of film of the nickel plating layer 9a or to effect an etching of the order of 5 nm to 10 nm by a nickel etchant on the surface of the nickel layer (buffer layer) 8a so as to remove impurities which hamper the adhesion between the nickel layer (buffer layer) 8a and the nickel plating layer 9a. While the solder connecting layer 5a is complete as the above, flash gold for example that becomes an antioxidant film of the nickel plating layer 9a may also be formed as the outermost layer for covering the surface of the solder connecting layer 5a.

With such construction, a heating device can be obtained as having a reliable solder connecting layer 5a which provides a sufficient adhesion to both the solder uniting layer (nickel plating layer) and the electrically insulating member and at the same time as capable of improving heat conducting performance. Also with such construction, a high level of adhesion can be secured between the solder connecting layer 5a and the electrically insulating member 2 that can sufficiently withstand warp occurring due to difference in coefficient of linear thermal expansion between the solder connecting layer 5a and the electrically insulating member 2 so that a high reliability can be achieved in a heating apparatus in which the heating device and a heated body are connected to each other with using a soft solder or a hard solder.

(Embodiment 2)

Figure 8:
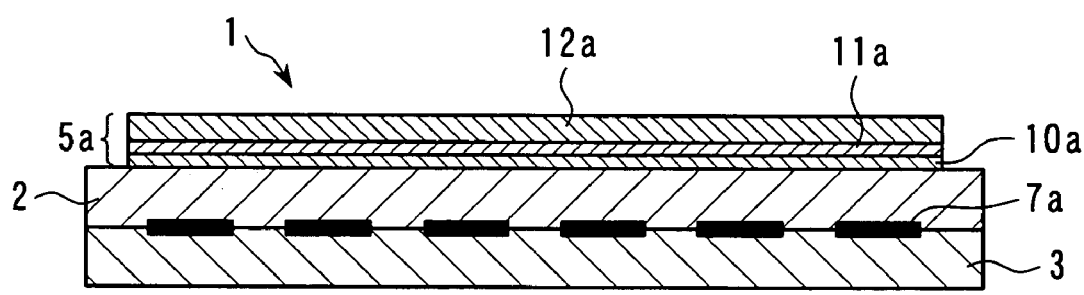
FIG. 8 is a sectional view showing the construction of a heating device according to a second embodiment of the invention.

A second embodiment will now be described. Since an overall construction of the present embodiment is similar to that of the first embodiment and only difference is in the construction of solder connecting layer, a description will be given below only with respect to the solder connecting layer. FIG. 8 is a sectional view of the heating device according to the present embodiment. As shown in FIG. 8, the solder connecting layer 5a is formed of a metal layer 10a serving as a lower buffer layer, a nickel layer 11a serving as an upper buffer layer and a nickel plating layer 12a serving as solder uniting layer.

Here a metal material having a favorable adhesion with the electrically insulating member 2 and the nickel layer (upper buffer layer) 11a, for example titanium or chromium that has a smaller free energy for oxide formation or nitride formation than nickel is preferably used as the material for forming the metal layer (lower buffer layer) 10a. These metals form an alloy layer at the portion toward the nickel layer 11a which is an upper buffer layer and improve adhesion between the metal layer (lower buffer layer) 10a and the nickel layer (upper buffer layer) 11a. On the other hand, for the electrically insulating member 2, these form an oxide or nitride of the metal layer (lower buffer layer) 10a between the metal layer (lower buffer layer) 10a and the electrically insulating member 2 to improve adhesion between the metal layer (lower buffer layer) 10a and the electrically insulating member 2. Further, since the nickel layer 11a serving as upper buffer layer is the base for forming film of the nickel plating layer 12a serving as solder uniting layer and their principal components are the same metal, adhesion between the nickel layer (upper buffer layer) 11a and the nickel plating layer (solder uniting layer) 12a is improved.

A method for forming the solder connecting layer 5a in the second embodiment will be briefly described below. First, on a surface corresponding to the heating section 1a of the electrically insulating member 2 holding the heating member 7, a metal layer 10a serving as lower buffer layer is formed for example with using titanium or chromium to a thickness of 10 nm to 500 nm by means of evaporation or sputtering method. Here it is desirable to effect plasma cleaning on the surface of the electrically insulating member 2 by an inert gas such as argon immediately before the forming of film of the metal layer (lower buffer layer) 10a to remove impurities which hamper adhesion between the metal layer (lower buffer layer) 10a and the electrically insulating member 2.

Next, the nickel layer 11a having a thickness of 10 nm to 500 nm is formed as upper buffer layer by means of evaporation or sputtering method on the metal layer (lower buffer layer) 10a. Here it is desirable to effect plasma cleaning on the surface of the metal layer (lower buffer layer) 10a with an inert gas such as argon immediately before the forming of film of the nickel layer (upper buffer layer) 11a so as to remove impurities which impede formation of alloy and hamper adhesion between the metal layer (lower buffer layer) 10a and the nickel layer (upper buffer layer) 11a.

The patterning of the metal layer (lower buffer layer) 10a and the nickel layer (upper buffer layer) 11a can be effected by the method in which deposition and patterning of the metal layer (lower buffer layer) 10a and nickel layer (upper buffer layer) 11a are concurrently effected at the time of evaporation or sputtering with using a shielding mask patterned into a desired configuration or by the method in which photo etching is effected after depositing the metal layer (lower buffer layer) 10a and nickel layer (upper buffer layer) 11a all over the front side of the electrically insulating member 2.

Also, the metal layer (lower buffer layer) 10a and nickel layer (upper buffer layer) 11a can be formed in succession with using the same apparatus.

Subsequently, a boron-contained nickel plating layer (Ni—B layer) 12a is formed as solder uniting layer on the nickel layer 11a to a thickness of 500 nm to 50 µm by an electrolytic or electroless method. The reason for this is that boron contained in the Ni—B layer makes less likely an occurrence of corrosion at the time of heat generation of the electrically insulating members 2 and 3 which are made for example of silicon nitride, aluminum nitride or aluminum oxide. It is desirable to effect plasma cleaning by an inert gas such as argon on the surface of the nickel layer (upper buffer layer) 11a immediately before the forming of film of the nickel plating layer 12a or to effect an etching of the order of 5 nm to 10 nm by a nickel etchant on the surface of the nickel layer (upper buffer layer) 11a so as to remove impurities which hamper adhesion between the nickel layer (upper buffer layer) 11a and the nickel plating layer 12a. While the solder connecting layer 5a is complete as the above, flash gold for example that becomes an antioxidant film of the nickel plating layer 12a may also be formed as the outermost layer for covering the surface of the solder connecting layer 5a.

With such construction, a further improvement is achieved in respect of adhesion between the buffer layer (metal layer and nickel layer) and the electrically insulating member as compared to the construction of the first embodiment so that a high level of adhesion can be secured between the solder connecting layer and the electrically insulating member that can sufficiently withstand warp occurring due to difference in coefficient of linear thermal expansion between the solder connecting layer and the electrically insulating member, and a high reliability can be achieved of a heating apparatus in which the heating device and a heated body are connected to each other with using a soft solder or a hard solder.

(Embodiment 3)

Figure 9:
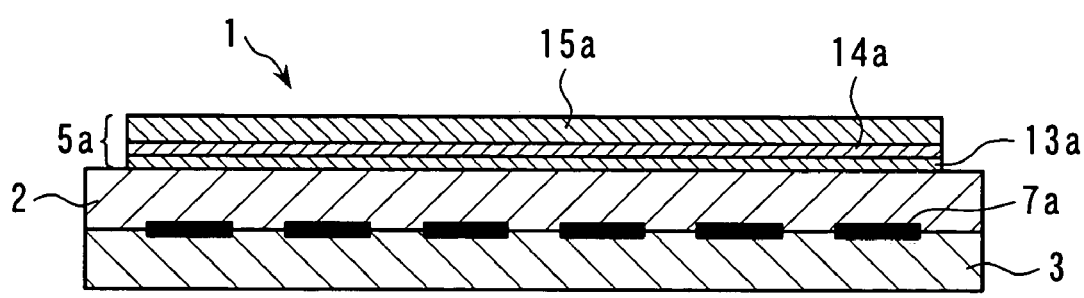
FIG. 9 is a sectional view showing the construction of a heating device according to a third embodiment of the invention.

A third embodiment will now be described. Since an overall construction of the present embodiment is similar to that of the first embodiment and only difference is in the construction of solder connecting layer, a description will be given below only with respect to the solder connecting layer. FIG. 9 is a sectional view of the heating device according to the present embodiment. As shown in FIG. 9, the solder connecting layer 5a is formed of a metal layer 13a serving as a lower buffer layer, a copper layer 14a serving as an upper buffer layer and a copper plating layer 15a serving as solder uniting layer.

Here a metal material having a favorable adhesion with the electrically insulating member 2 and the copper layer (upper buffer layer) 14a, for example titanium or chromium that has a smaller free energy for oxide formation or nitride formation than nickel is preferably used as the material for forming the metal layer (lower buffer layer) 13a. These metals form an alloy layer at the portion toward the copper layer 14a which is an upper buffer layer and improve adhesion between the metal layer (lower buffer layer) 13a and the copper layer (upper buffer layer) 14a. On the other hand, for the electrically insulating member 2, these form an oxide or nitride of the metal layer (lower buffer layer) 13a between the metal layer (lower buffer layer) 13a and the electrically insulating member 2 to improve adhesion between the metal layer (lower buffer layer) 13a and the electrically insulating member 2. Further, since the copper layer 14a serving as upper buffer layer is the base for forming film of the copper plating layer 15a serving as solder uniting layer and their principal components are the same metal, adhesion between the copper layer (upper buffer layer) 14a and the copper plating layer (solder uniting layer) 15a is improved.

A method for forming the solder connecting layer 5a in the third embodiment will be briefly described below. First, on a surface corresponding to the heating section 1a of the electrically insulating member 2 holding the heating member 7, a metal layer 13a serving as lower buffer layer is formed for example with using titanium or chromium to a thickness of 10 nm to 200 nm by means of evaporation or sputtering method. Here it is desirable to effect plasma cleaning on the surface of the electrically insulating member 2 by an inert gas such as argon immediately before the forming of film of the metal layer (lower buffer layer) 13a to remove impurities which hamper adhesion between the metal layer (lower buffer layer) 13a and the electrically insulating member 2.

Next, the copper layer 14a having a thickness of 10 nm to 200 nm is formed as upper buffer layer by means of evaporation or sputtering method on the metal layer (lower buffer layer) 13a. Here it is desirable to effect plasma cleaning on the surface of the metal layer (lower buffer layer) 13a with an inert gas such as argon immediately before the forming of film of the copper layer (upper buffer layer) 14a so as to remove impurities which impede formation of alloy and hamper adhesion between the metal layer (lower buffer layer) 13a and the copper layer (upper buffer layer) 14a.

The patterning of the metal layer (lower buffer layer) 13a and the copper layer (upper buffer layer) 14a can be effected by the method in which deposition and patterning of the metal layer (lower buffer layer) 13a and copper layer (upper buffer layer) 14a are concurrently effected at the time of evapration or sputtering with using a shielding mask patterned into a desired configuration or by the method in which photo etching is effected after depositing the metal layer (lower buffer layer) 13a and copper layer (upper buffer layer) 14a all over the front side of the electrically insulating member 2. Also, the metal layer (lower buffer layer) 13a and copper layer (upper buffer layer) 14a can be formed in succession with using the same apparatus.

Subsequently, a copper plating layer 15a is formed as solder uniting layer on the copper layer 14a to a thickness of 500 nm to 50 µm by an electrolytic or electroless method. Here, since diffusion of a soft solder or a hard solder at high temperature into the copper plating layer 15a is smaller than the diffusion into a nickel plating layer, it is possible to achieve a longer life of adhesion between the soft solder or hard solder and the solder connecting layer. While the solder connecting layer 5a is complete as the above, flash gold for example that becomes an antioxidant film of the copper plating layer 15a may also be formed as the outermost layer for covering the surface of the solder connecting layer 5a.

With such construction, a longer life of adhesion is achieved between a soft solder or a hard solder and the solder connecting layer 5a and a further improvement is achieved with respect to adhesion between the buffer layer (metal layer and copper layer) and the electrically insulating member as compared to the construction of the first embodiment. Accordingly, a high level of adhesion can be secured between the solder connecting layer and the electrically insulating member that can sufficiently withstand warp occurring due to difference in coefficient of linear thermal expansion between the solder connecting layer and the electrically insulating member, and a high reliability can be achieved of a heating apparatus in which the heating device and a heated body are connected to each other with using a soft solder or a hard solder.

While examples of constructing the buffer layer of the solder connecting layer by two layers have been described in the above second and third embodiments, the buffer layer is not limited to the two-layer construction and can be formed to have three or more layers. In such case, a material having a coefficient of linear thermal expansion not substantially different from and its value located between the coefficients of linear thermal expansion of the electrically insulating member and the solder uniting layer (nickel plating layer or copper plating layer) is preferably selected as the buffer layer.

(Embodiment 4)

Figure 10:
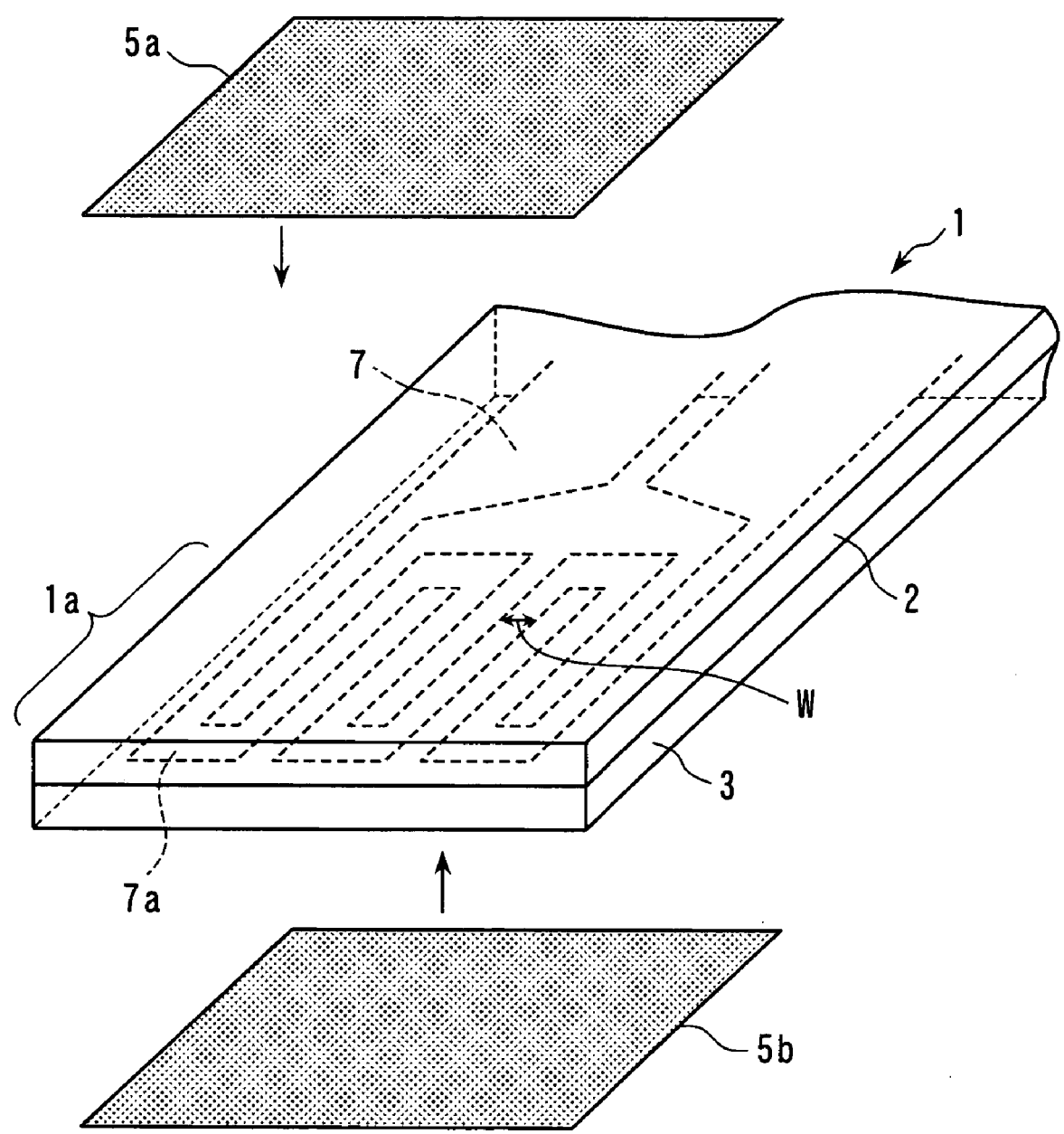
FIG. 10 is a perspective view showing the construction of a heating device according to a fourth embodiment of the invention with separating solder connecting layers therefrom.
Figure 11:
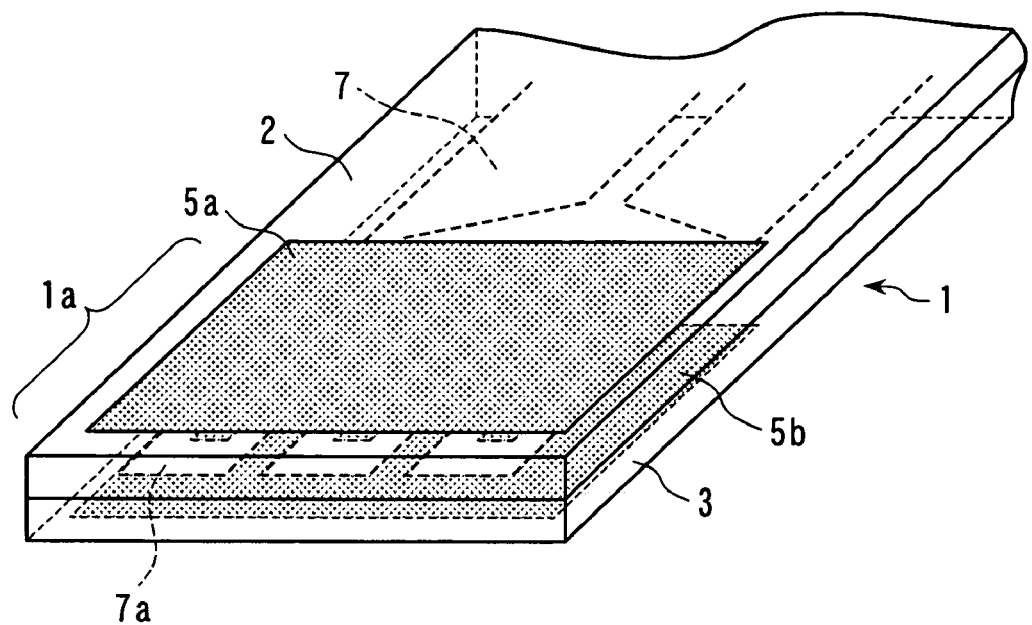
FIG. 11 is a perspective view of the construction of the heating section of the heating device according to the fourth embodiment shown in FIG. 10 with the solder connecting layer joined thereto.

A fourth embodiment will now be described. In the present embodiment, a description will be given with respect to a heating device having a solder connecting layer formed on both sides of the electrically insulating member which holds a heating member and a heating method using the heating device. FIGS. 10 and 11 each are a perspective view showing a heating device according to the present embodiment. In FIG. 10, it is shown with the solder connecting layers separated therefrom. An example of mounting the heating device on a heated body is shown in FIG. 12.

Figure 12:
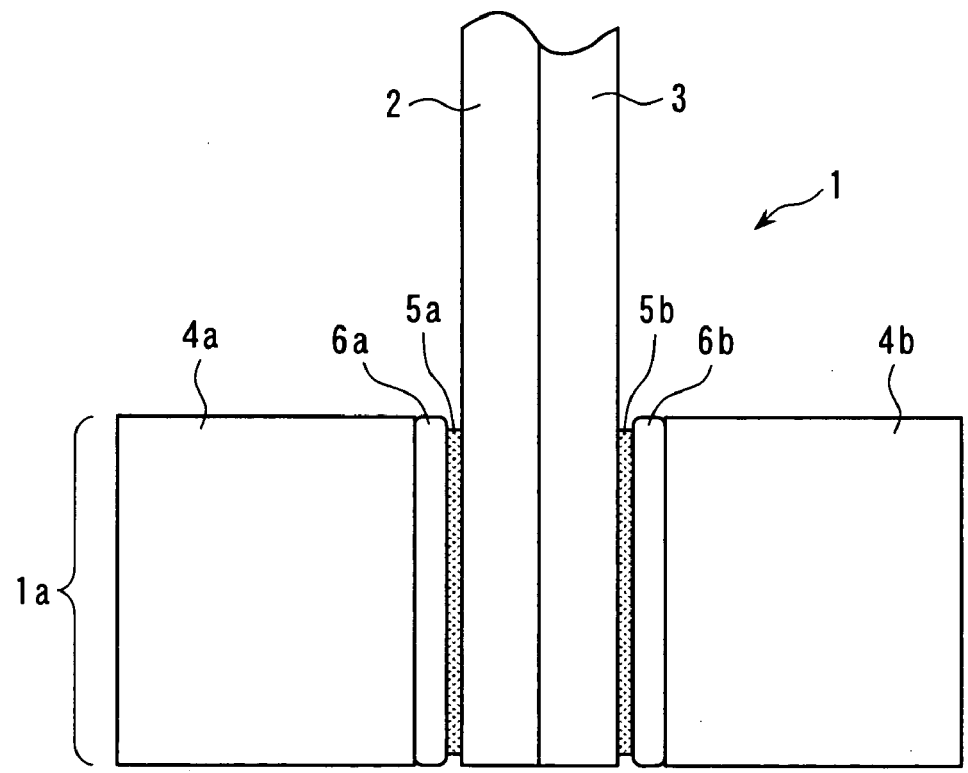
FIG. 12 shows the manner where a heated body is mounted as connected by means of a heat conducting layer to the heating device according to the fourth embodiment shown in FIG. 11.

A heating device 1 having solder connecting layers 5a and 5b formed on both sides of the electrically insulating members 2 and 3 holding a heating member 7 as shown in FIGS. 10 and 11 is mounted on heated body 4a and 4b as shown in FIG. 12. Here, the connection between the heating device 1 and the heated body 4a, 4b, i.e., connection between the solder connecting layer 5a, 5b and the heated body 4a, 4b is effected through a heat conducting layer 6a, 6b. The heat conducting layer 6a, 6b is a soft solder or a hard solder of an alloy having a favorable heat conducting performance and efficiently transmits heat generated at the heating section 1a of the heating device 1 to the heated body 4, 4b. As previously described, on the other hand, the heating member 7 for example of nickel-chromium or a high melting point metal such as molybdenum or tungsten is held by the electrically insulating members 2 and 3 and is narrowed in its width W and elongated to have a slender section 7a within the heating section 1a so as to increase resistance value and facilitate heat generation at the region of the heating section 1a in the heating device 1.

By thus providing the solder connecting layers 5a, 5b on the both sides of the electrically insulating members 2, 3 holding the heating member 7 so as to connect the solder connecting layer 5a, 5b and the heated body 4a, 4b to each other through the heat conducting layer 6a, 6b, the heat conducting area to the heated body 4a, 4b is increased so that an efficient heat conduction is effected to improve the heat conducting performance to the heated body 4a, 4b. Further, a high temperature-rising characteristic of the heated body 4a, 4b is achieved.

As the above, according to the invention, a heating device having a reliable solder connecting layer having a sufficient adhesion to both a solder uniting layer and an electrically insulating member and at the same time capable of improving heat conducting performance can be achieved by forming the solder connecting layer into a laminate structure. Further it is possible to achieve a high level of adhesion between the solder connecting layer and the electrically insulating member that can sufficiently withstand warp due to difference in coefficient of linear thermal expansion between the heat conducting layer and the solder connecting layer as well as the electrically insulating member resulting from connection between the heating device and the heated body using the heat conducting layer which is made of a soft solder or a hard solder. Furthermore, by providing a solder connecting layer and heat conducting layer on both sides of the heating section of the heating device, a heat conducting performance to the heated body can be improved and it is possible to obtain a high level of temperature rising characteristic of the heated body and a high reliability of a heating apparatus which is formed by connecting the heating device and the heated body.

What is claimed is:

1. A heating device comprises a heating member held in an electrically insulating member and a solder connecting layer for connecting a heated body formed on a surface of said electrically insulating member corresponding to at least a portion of said heating member to improve a heat conducting performance from the heating member to the heated body connected thereto through a heat conducting layer, said solder connecting layer comprising a laminated structure, wherein said solder connecting layer comprises at least one buffer layer and a solder uniting layer.

2. The heating device according to claim 1, wherein said buffer layer comprises a metal layer.

3. The heating device according to claim 1 or 2, wherein said solder uniting layer comprises a nickel plating layer or copper plating layer.

4. The heating device according to claim 2, wherein said solder connecting layer is formed on at least one side of said electrically insulating member.

5. The heating device according to claim 1, wherein said solder connecting layer is formed on at least one side of said electrically insulating member.

6. The heating device according to claim 2, wherein said solder connecting layer is formed on at least one side of said electrically insulating member.

7. The heating device according to claim 3, wherein said solder connecting layer is formed on at least one side of said electrically insulating member.

* * * * *